United States Patent
Vieira et al.

(10) Patent No.: US 9,121,813 B2
(45) Date of Patent: Sep. 1, 2015

(54) AUTOMATIC MORPHOMETRY AND CLASSIFICATION OF CRYSTALS OF IRON OXIDES

(71) Applicants: VALE S.A., Rio de Janeiro (BR); FACULDADES CATÓLICAS, Rio de Janeiro (BR)

(72) Inventors: Maria Beatriz Vieira, Nova Lima (BR); Sidnei Paciornik, Rio de Janeiro (BR); Otavio de Fonseca Martins Gomes, Rio de Janeiro (BR); Júlio Cesar Álvarez Iglesias, Rio de Janeiro (BR); Aloísio Antônio Melo Borges, Belo Horizonte (BR)

(73) Assignees: VALE S.A., Rio de Janerio (BR); FACULDADES CATOLICAS, Rio de Janerio (BR)

( * ) Notice: Subject to any disclaimer, the term of this patent is extended or adjusted under 35 U.S.C. 154(b) by 79 days.

(21) Appl. No.: 14/038,428

(22) Filed: Sep. 26, 2013

(65) Prior Publication Data
US 2014/0093137 A1    Apr. 3, 2014

Related U.S. Application Data

(60) Provisional application No. 61/707,695, filed on Sep. 28, 2012.

(51) Int. Cl.
*G01N 21/21* (2006.01)
*G06T 7/00* (2006.01)
*G06K 9/00* (2006.01)

(52) U.S. Cl.
CPC .............. *G01N 21/21* (2013.01); *G06K 9/0014* (2013.01); *G06T 7/0081* (2013.01)

(58) Field of Classification Search
CPC ................... G01N 33/54346; G01N 21/1717; G01N 21/21; A61K 33/26; C04B 2237/123
See application file for complete search history.

(56) References Cited

PUBLICATIONS

Pirard et al., "Particle texture analysis using polarized light imaging and grey level intercepts," 2007, International Journal of Mineral Processing 84, pp. 299-309.*

* cited by examiner

*Primary Examiner* — Amir Alavi
*Assistant Examiner* — Kenny Cese
(74) *Attorney, Agent, or Firm* — Arent Fox LLP

(57) ABSTRACT

An automatic method for the classification of crystals of iron oxides, including the measurement of oxide crystal size and shape, by a digital microscopy procedure involving image acquisition, processing, analysis, and classification is described.

28 Claims, 2 Drawing Sheets

AUTOMATIC MORPHOMETRY AND CLASSIFICATION OF CRYSTALS OF IRON OXIDES

This application claims priority from U.S. Patent Application No. 61/707,695, entitled "Automatic Morphometry and Classification of Hematite," filed on Sep. 28, 2012, which is incorporated herein by reference in its entirety.

FIELD OF THE INVENTION

The present invention refers to an automatic method for the classification of iron ores, including the measurement of crystal size and shape, by a digital microscopy procedure involving image acquisition, processing, analysis, and classification.

BACKGROUND OF THE INVENTION

The mineralogic constitution of iron ores, the classification of oxides morphology types, and crystal size measurement allow for quantifying detailed intrinsic characteristics of iron ores in a way that is not provided by any other conventional method. Some of these parameters are usually obtained on an optical microscope by a visual estimate, but in a very labor intensive procedure, with results prone to strong variability.

Classification of iron ores, their crystal size, and shape are relevant parameters in geometallurgical processes for the steel making industry. These parameters have been defined and applied by Vale since the 1990's. Traditionally, this analysis is done by an experienced human operator observing cross sections of ore samples under an optical microscope. This procedure is at most semi-quantitative, is strongly operator dependent and prone to errors and lack of reproducibility.

SUMMARY OF THE INVENTION

This invention aims to overcome this scenario by proposing an automatic method for the classification of iron oxides, mainly hematite, including the measurement of crystal size and shape, by a digital microscopy procedure involving image acquisition, processing, analysis, and classification as described herein.

More specifically, the present invention describes an automatic method for the classification of crystals of iron oxides comprising the steps of:
  a) Image acquisition; and
  b) Analysis method
wherein the analysis method b is divided into a synthetic step i followed by an analytic step ii.

DESCRIPTION OF PREFERRED EMBODIMENTS

The following detailed description does not intend to, in any way, limit the scope, applicability or configuration of the invention. More exactly, the following description provides the necessary understanding for implementing the exemplary modalities. When using the teachings provided herein, those skilled in the art will recognize suitable alternatives that can be used, without extrapolating the scope of the present invention.

Figure 1:
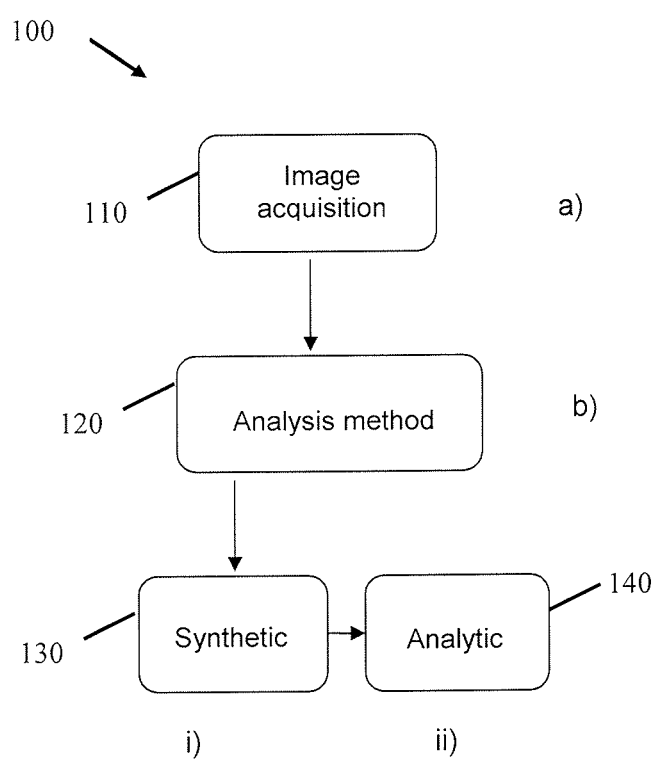
FIG. 1 is a flowchart of the automatic method provided by the present invention.
Figure 2:
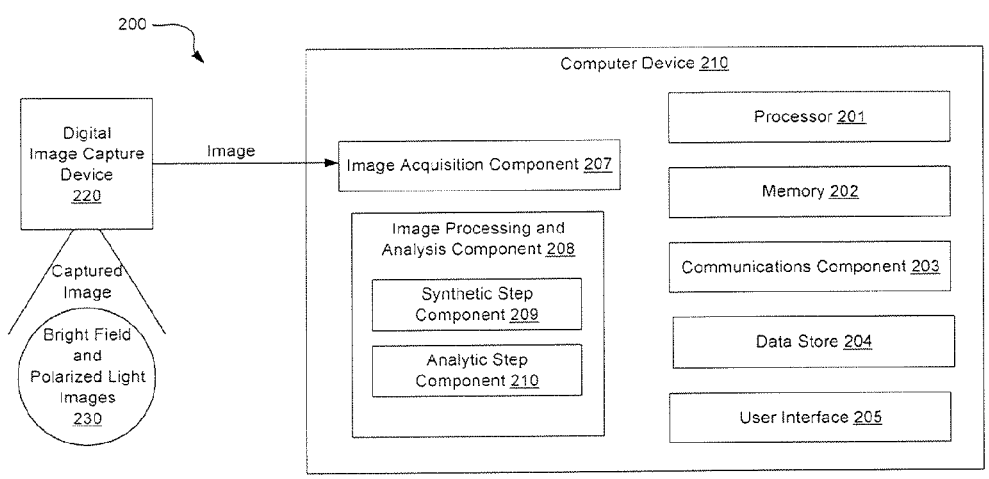
FIG. 2 is a system, including a computer device having components configured to perform aspects of the automatic method provided by the present invention.

Referring to FIGS. 1 and 2, the present invention describes an automatic method 100 for the classification of crystals of iron oxides comprising the steps of:
  a. image acquisition (110); and
  b. a processing and analysis method (120)

In one of the embodiments of the present invention, the iron ore consists in hematite.

A system 200, including a computer device 210, may be configured to perform aspects of an automatic method 100 for the classification of crystals of iron oxides.

The system 200 includes digital image capture device 220, such as, for example, a digital camera, which captures Bright Field (BF) and Polarized Light images 230 in reflection mode. For example, an optical microscope operating in reflected light mode and including a fixed entry polarizer and a rotating exit polarizer (the analyzer) or a system for circular polarization can be used to capture these images, using a suitable digital camera. The microscope should be computer-controlled and motorized so that the imaging mode (BF, LPOL or CPOL) can be selected by a suitable software routine.

The system 200 also includes a computer device 210, which, at 110 of method 100, acquires the captured image, e.g., via an image acquisition component 207 from the digital image capture device 220.

Although the digital image capture device 220 and the digital image acquisition component 207 are shown as separate components, they can be part of the same component. For example, digital image capture device 220 can be part of a computer device, such as the example of computer device 210, that also includes some or all of the other components shown in the example of computer device 210. In another example, some or all of the components shown in the example of computer device 210 may be included as part of digital image capture device 220.

Polarized images can be captured in one of two modes: linearly (LPOL) or circularly polarized (CPOL) light. In LPOL the entry polarizer and the exit analyzer are positioned close to the extinction condition (crossed polarizer). Either one image (LPOL) at a given angle, or a pair of images (LPOL+, LPOL−) at symmetrical angles from the extinction position, are acquired. In CPOL a single image is captured with circular polarization.

The computer device 210, at 120 of method 100, performs a processing and analysis method, e.g., via an image processing and analysis component 208, which may be software and/or hardware executing one or more of a processing and analysis algorithm or function, on the BF image and either the LPOL, or the (LPOL+, LPOL−) image pair, or the CPOL image.

The processing and analysis method, step b (120) has a hierarchical approach which is divided into two steps:
  i. synthetic (130) and
  ii. analytic (140).

The computer device 210, at 130 of method 100, analyzes, e.g., via synthetic step component 209 which may be software and/or hardware executing one or more of a synthetic algorithm or function, each image field and discriminates two domains of hematite: a domain comprising the compact types (here named granular, lamellar, lobular), and a domain comprising the porous textures (including the microcrystalline crystals and martite).

The computer device 210, at 140 of method 100, discriminates, measures, and classifies individual crystals according to their morphology, for example as granular, lamellar, or lobular e.g., via an analytic step component 210, which may be software and/or hardware executing one or more of an analytic algorithm or function.

The computer device 610 also may include a processor 601 for carrying out processing functions associated with one or more of the components and functions described herein. The processor 601 can include a single or multiple set of processors or multi-core processors. Moreover, the processor 601 can be implemented as an integrated processing system and/or a distributed processing system.

The computer device 610 also may include a memory 602, such as for storing data used herein and/or local versions of applications being executed by processor 601. The memory 602 can include any type of memory usable by a computer, such as random access memory (RAM), read only memory (ROM), tapes, magnetic discs, optical discs, volatile memory, non-volatile memory, and any combination thereof.

The computer device 610 also may include a communications component 603 that provides for establishing and maintaining communications with one or more entities utilizing hardware, software, and services as described herein. The communications component 603 may carry communications between components within the computer device, as well as between the computer device and external devices, such as devices located across a communications network and/or devices serially or locally connected to the computer device. For example, the communications component 603 may include one or more buses, and may further include transmit chain components and receive chain components associated with one or more transmitters and receivers, respectively, or one or more transceivers, operable for interfacing with external devices.

The computer device 610 also may include a data store 604, which can be any suitable combination of hardware and/or software, that provides for mass storage of information, databases, and programs employed in connection with aspects described herein. For example, the data store 604 may be a data repository for applications not currently being executed by the processor 601.

The computer device 610 also may include a user interface component 605 operable to receive inputs from a user of the computer device 610, and further operable to generate outputs for presentation to the user. The user interface component 605 may include one or more input devices, including but not limited to a keyboard, a number pad, a mouse, a touch-sensitive display, a navigation key, a function key, a microphone, a voice recognition component, any other mechanism capable of receiving an input from a user, or any combination thereof. Further, the user interface component 605 may include one or more output devices, including but not limited to a display, a speaker, a haptic feedback mechanism, a printer, any other mechanism capable of presenting an output to a user, or any combination thereof.

More particularly, and in an example, the synthetic step i comprises the measurement of image texture based on Haralick parameters. The BF image is segmented by a conventional threshold selection method, so that only iron ores regions are preserved. These regions are used as a mask for the LPOL or CPOL images. These masked images are divided into square regions (textels) and the 11 first Haralick parameters are measured for each textel. These values are measured in 4 directions (0, 45, 90, and 135 degrees) and their average and range values are obtained. The measured values are used as discriminant features in a supervised classification procedure that is able to discriminate between the 5 types with success rates above 99%. The result of the synthetic step i is the classification of each image textel into one of the 5 types of iron ores, and the measurement of area fraction occupied by each type.

The textures identified by the synthetic step i as belonging to the 3 compact types (granular, lamellar, or lobular) are submitted to the analytic step ii. This step comprises a method which involves the detection of individual crystal boundaries. This method uses the Canny algorithm to detect incomplete iron ores crystal edges on the polarized image or images. It then uses a watershed algorithm to connect edges and form closed contours. These closed contours define regions that undergo ultimate erosion until they are transformed into single pixel seeds. These seeds are used as input to a modified region growing algorithm.

Iron Ores crystals are reconstructed based on the seeds positions and on the two LPOL images or the single CPOL image. The spectral distance $d^g(x,y)$ is calculated between each pixel $p(x,y)$ connected to crystal g and the value of its seed $p(x_g,y_g)$ in the CPOL image (or in the two LPOL images). If this distance (or the maximum between the two distances in the LPOL case) is smaller than a given threshold t, the pixel $p(x,y)$ belongs to crystal g.

In the case of LPOL the spectral distance is defined as:

$$d^g(x, y) = \text{Max}(d_1^g(x, y), d_2^g(x, y)) \quad (1)$$

$$d_i^g(x, y) = \sqrt{\frac{(R_i(x, y) - R_i(x_g, y_g))^2 + (G_i(x, y) - G_i(x_g, y_g))^2 +}{(B_i(x, y) - B_i(x_g, y_g))^2}} \quad (2)$$

Where i=1 or 2, refers to the 2 LPOL images; $R_i(x,y)$, $G_i(x,y)$, $B_i(x,y)$ are the RGB values of pixel $p(x,y)$ in the LPOL image i; $R_i(x_g,y_g)$, $G_i(x_g,y_g)$, $B_i(x_g,y_g)$ are the RGB values of pixel $p(x_g,y_g)$ in image LPOL i.

In the CPOL case, the spectral distance is based on a single image as:

$$d^g(x, y) = \sqrt{\frac{(R(x, y) - R(x_g, y_g))^2 + (G(x, y) - G(x_g, y_g))^2 +}{(B(x, y) - B(x_g, y_g))^2}} \quad (3)$$

where $R(x,y)$, $G(x,y)$, $B(x,y)$ are the RGB values of pixel $p(x,y)$ in the CPOL image; and $R(x_g,y_g)$, $G(x_g,y_g)$, $B(x_g,y_g)$ are the RGB values of pixel $p(x_g,y_g)$ in the CPOL image.

Once the GIP algorithm ends, individual crystals are identified and labeled.

Size and shape parameters of the individual crystals are measured and used as features in a supervised classification procedure that is able to attribute a specific class (here named as granular, lamellar or lobular) to each crystal with success rates above 97%.

The image analysis of iron ores gives quantitative results with higher precision and in a shorter time, and is applicable, for instance, to geometallurgical processes that look for correlation between iron ores characteristics and its behavior in the concentration unit in mining operations, or in agglomeration and reduction processes in the steel making industry.

The main differences between the current and proposed technologies are summarized in the Table 1 below:

TABLE 1

Main differences between the current and proposed technologies.

| Current Technology | New Technology |
| --- | --- |
| Human operator visually identifies iron minerals | Automatic system identifies iron minerals |
| Human operator visually estimates the area fraction of each iron oxide type | Automatic system measures the area fraction of each iron oxide type |
| Human operator visually estimates crystal sizes for the compact hematite crystal types | Automatic system measures crystal sizes for the compact hematite crystal types |
| Subjective method | Objective and reproducible method |
| Strongly operator dependent | Independent of operator |
| Manual microscopy system | Automated microscopy system |

As used in this application, the terms "component," "module," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Additionally, at least one processor may comprise one or more modules operable to perform one or more of the steps and/or actions described above.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of codes and/or instructions on a machine readable medium and/or computer readable medium, which may be incorporated into a computer program product.

In one or more aspects, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection may be termed a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs usually reproduce data optically with lasers. Combinations of the above should also be included within the scope of computer-readable media.

The invention claimed is:

1. An automatic method for classifying crystals of iron oxides comprising:
   acquiring images of an iron ore, wherein the acquired images comprise a bright field image (BF) and one or more polarized light image in reflection mode; and
   processing and analyzing the acquired images,
   wherein the processing and analyzing of the acquired images comprises a synthetic step followed by an analytic step.

2. The method of claim 1, wherein the polarized light image is captured in at least one of the modes selected from a group consisting of a linear mode (LPOL) and a circularly polarized light mode (CPOL).

3. The method of claim 2, wherein in LPOL, an entry polarizer and an exit analyzer are positioned close to an extinction condition.

4. The method of claim 2, wherein the acquiring includes acquiring an image in LPOL at a predetermined angle or a pair of images at symmetrical angles from an extinction position.

5. The method of claim 2, wherein in CPOL, a single image is captured with circular polarization.

6. The method of claim 2, wherein the one or more polarized light image is an image captured in the LPOL, an image pair captured in the LPOL, or an image captured in CPOL.

7. The method of claim 1, wherein acquiring the images is performed by an optical microscope operating in a reflected light mode, including a fixed entry polarizer and a rotating exit polarizer or a system for circular polarization and a digital camera.

8. The method of claim 7, wherein the optical microscope is computer controlled and motorized and the imaging mode (BF, LPOL, CPOL) is selected by software.

9. The method of claim 2, comprising segmenting the BF by a threshold selection method to identify regions of hematite and preserving the regions of hematite.

10. The method of claim 9, comprising applying the preserved regions of hematite as a mask to the one or more polarized light image captured in LPOL or CPOL to form one or more masked image.

11. The method of claim 10, wherein the masked image is divided into square regions (textels) and Haralick parameters are measured for each textel.

12. The method of claim 11, wherein the Haralick parameters are measured in 4 directions.

13. The method of claim 12, wherein the 4 directions are 0, 45, 90, and 135 degrees.

14. The method of claim 1, wherein the method is a reproducible method.

15. The method of claim 1, wherein the method is independent of an operator.

16. The method of claim 1, wherein the iron ore comprises hematite as a constituent mineral.

17. An automatic method for classifying crystals of iron oxides comprising:
   acquiring one or more image of an iron ore; and
   processing and analyzing the acquired one or more image, wherein the processing and analyzing of the acquired one or more image comprises a synthetic step followed by an analytic step, wherein the synthetic step analyzes one or more image field of an acquired image and identifies the one or more image field as a morphology of iron oxide selected from a group consisting of granular, lamellar, lobular, microcrystalline, and matte.

18. The method of claim 17, wherein the one or more image field is identified as granular, lamellar, or lobular and is submitted to the analytic step.

19. The method of claim 17, wherein the synthetic step comprises measuring image texture based on Haralick parameters.

20. The method of claim 18, wherein the analytic step comprises the detection of individual crystal boundaries by a Canny algorithm.

21. The method of claim 18, wherein the analytic step uses a watershed algorithm.

22. The method of claim 21, wherein closed contours formed by the watershed algorithm undergoes ultimate erosion until they are transformed into single pixel seeds.

23. The method of claim 22, wherein the seeds are used as an input to a modified region growing algorithm.

24. An automatic method for classifying crystals of iron oxides comprising:
   acquiring one or more image, wherein the acquired one or more image comprises two polarized light images captured in a linear mode (LPOL) or an image captured in a circularly polarized light mode (CPOL); and
   processing and analyzing the acquired one or more image, comprising a synthetic step followed by an analytic step, wherein the analytic step uses a watershed algorithm to form closed contours that undergo ultimate erosion until transformed into single pixel seeds, the single pixel seeds being used as an input to a modified region growing algorithm, wherein crystals of iron oxides are reconstructed based on positions of the single pixel seeds and on the acquired one or more image.

25. The method of claim 24, wherein a spectral distance $d^g(x,y)$ is calculated between each pixel $p(x,y)$ connected to a crystal g and a value of its seed $p(x_g,y_g)$ in the CPOL image or in the two LPOL images.

26. The method of claim 25, wherein when the acquired one or more image comprises two polarized light images captured in the LPOL, if distance, or a maximum between two distances is smaller than a given-threshold t, the pixel $p(x,y)$ belongs to crystal g.

27. The method of claim 25, wherein when the acquired one or more image comprises two polarized light images captured in the LPOL, the spectral distance is defined as:

$$d^g(x, y) = \text{Max}(d_1^g(x, y), d_2^g(x, y)) \quad (1)$$

$$d_i^g(x, y) = \sqrt{(R_i(x, y) - R_i(x_g, y_g))^2 + (G_i(x, y) - G_i(x_g, y_g))^2 + (B_i(x, y) - B_i(x_g, y_g))^2}$$

where i=1 or 2 and refers to the 2 LPOL images; $R_i(x,y)$, $G_i(x,y)$, $B_i(x,y)$ are RGB values of pixel $p(x,y)$ in the LPOL image i; $R_i(x_g,y_g)$, $G_i(x_g,y_g)$, $B_i(x_g,y_g)$ are RGB values of pixel $p(x_g,y_g)$ in image LPOL i.

28. The method of claim 25, wherein when the acquired one or more image comprises a polarized light image captured in the CPOL, the spectral distance is based on a single image as:

$$d^g(x, y) = \sqrt{(R(x, y) - R(x_g, y_g))^2 + (G(x, y) - G(x_g, y_g))^2 + (B(x, y) - B(x_g, y_g))^2}$$

where R(x,y), G(x,y), B(x,y) are RGB values of pixel $p(x,y)$ in the CPOL image; and
$R(x_g,y_g)$, $G(x_g,y_g)$, $B(x_g,y_g)$ are RGB values of pixel $p(x_g,y_g)$ in the CPOL image.

* * * * *